(12) United States Patent
Marschall et al.

(10) Patent No.: US 10,328,169 B2
(45) Date of Patent: Jun. 25, 2019

(54) SYSTEM FOR INTRODUCING FRAGRANCES INTO THE INTERIOR OF A VEHICLE

(71) Applicants: Enquiry Eye GmbH, Munster (DE); Bayerische Motoren Werke, München (DE)

(72) Inventors: Ursula Marschall, Munster (DE); Erhan Ergen, Munich (DE); Andreas Menne, Fröndenberg (DE)

(73) Assignee: Bayerische Motoren Werke Aktiengesellschaft, Munich (DE)

( * ) Notice: Subject to any disclaimer, the term of this patent is extended or adjusted under 35 U.S.C. 154(b) by 480 days.

(21) Appl. No.: 14/432,879

(22) PCT Filed: Oct. 2, 2013

(86) PCT No.: PCT/EP2013/070538
§ 371 (c)(1),
(2) Date: Apr. 1, 2015

(87) PCT Pub. No.: WO2014/053539
PCT Pub. Date: Apr. 10, 2014

(65) Prior Publication Data
US 2015/0290350 A1 Oct. 15, 2015

(30) Foreign Application Priority Data
Oct. 2, 2012 (DE) .................. 10 2012 019 332

(51) Int. Cl.
*A61L 2/23* (2006.01)
*B60H 3/00* (2006.01)
*B60H 3/06* (2006.01)
*B01D 46/00* (2006.01)
*B01D 46/10* (2006.01)
*B01D 46/52* (2006.01)

(52) U.S. Cl.
CPC ............ *A61L 2/23* (2013.01); *B01D 46/0038* (2013.01); *B01D 46/10* (2013.01); *B01D 46/525* (2013.01); *B60H 3/0014* (2013.01); *B60H 3/06* (2013.01); *B60H 3/0608* (2013.01)

(58) Field of Classification Search
None
See application file for complete search history.

(56) References Cited

U.S. PATENT DOCUMENTS 2,352,075 A * 6/1944 Brownstein ............... A61L 9/12
206/0.5
2,438,129 A * 3/1948 Rich ....................... A24F 25/02
222/544

(Continued)

*Primary Examiner* — Duane Smith
*Assistant Examiner* — Brit E. Anbacht
(74) *Attorney, Agent, or Firm* — Brooks Kushman P.C.

(57) ABSTRACT

The invention relates to a system for introducing fragrances into the interior of a vehicle via the ventilation system comprising a combination of a fragrance cartridge (2) and an air filter (1), wherein the fragrance cartridge (2) has at least one air inlet opening (3) and at least one air outlet opening (4), as well as a space (17) accommodating a fragrance-emanating substrate, wherein the fragrance cartridge (2) is secured to the air filter (1) in such a manner that air passes through the fragrance cartridge (2) when the ventilation system has been activated.

6 Claims, 5 Drawing Sheets

(56) References Cited

U.S. PATENT DOCUMENTS

| | | | | |
|---|---|---|---|---|
| 4,279,373 | A * | 7/1981 | Montealegre | B65D 5/38 206/0.5 |
| 4,617,157 | A * | 10/1986 | Stein | A61L 9/12 239/57 |
| 4,813,344 | A * | 3/1989 | Greif | A61L 9/12 239/58 |
| 5,240,487 | A * | 8/1993 | Kung | A61L 9/12 261/DIG. 88 |
| 5,478,505 | A * | 12/1995 | McElfresh | A61L 9/122 239/57 |
| 7,892,333 | B2 * | 2/2011 | Elliot | B01D 46/0028 261/DIG. 88 |
| 8,978,998 | B1 * | 3/2015 | Talley | A61L 9/127 239/51.5 |
| 2002/0197187 | A1 * | 12/2002 | Murray | A61L 9/12 422/124 |
| 2005/0103880 | A1 * | 5/2005 | Taite | A61L 9/12 239/57 |
| 2005/0224595 | A1 * | 10/2005 | Kuiper | A47L 7/04 239/59 |
| 2006/0236869 | A1 * | 10/2006 | Giraud | A61L 9/12 96/222 |
| 2011/0139646 | A1 * | 6/2011 | Sonnenberg | A45D 27/225 206/352 |
| 2012/0024974 | A1 * | 2/2012 | Grodsky | A61L 9/037 239/6 |
| 2012/0079945 | A1 * | 4/2012 | Roberts | B01D 46/0038 96/222 |

\* cited by examiner

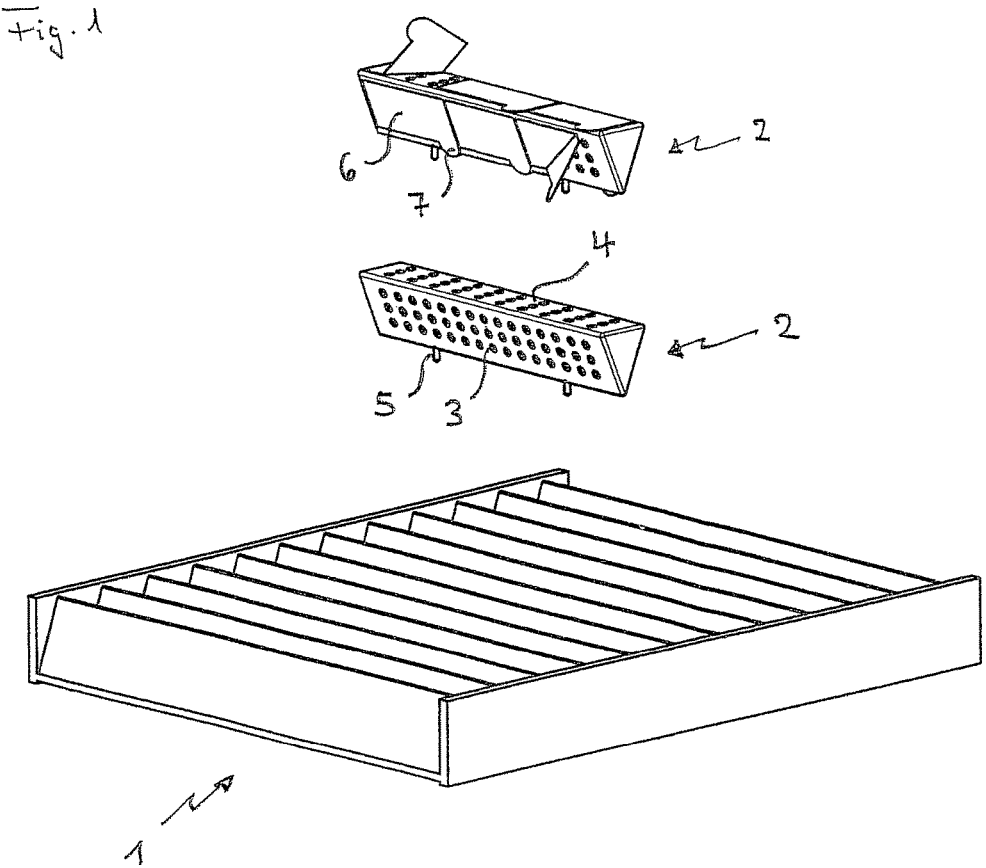

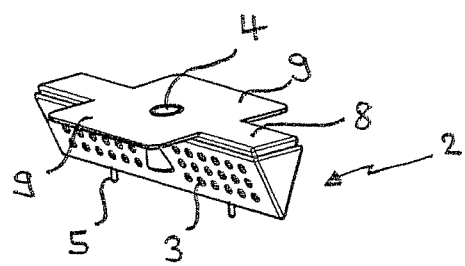
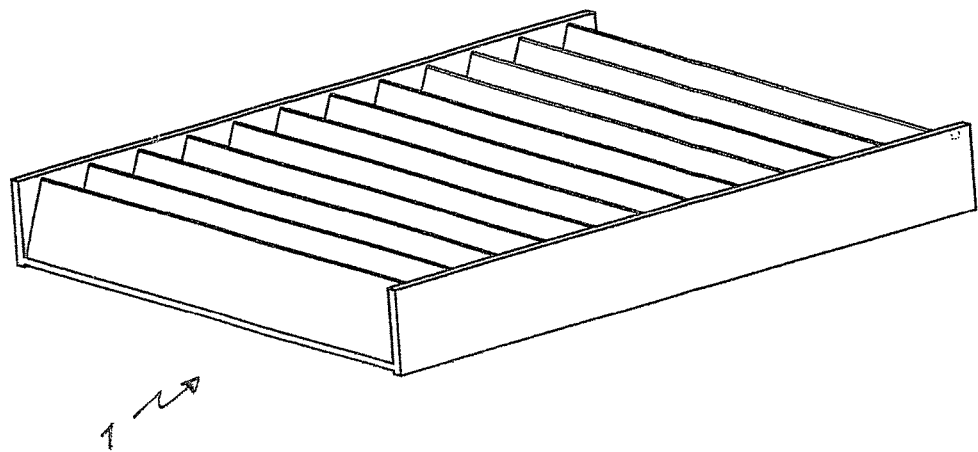

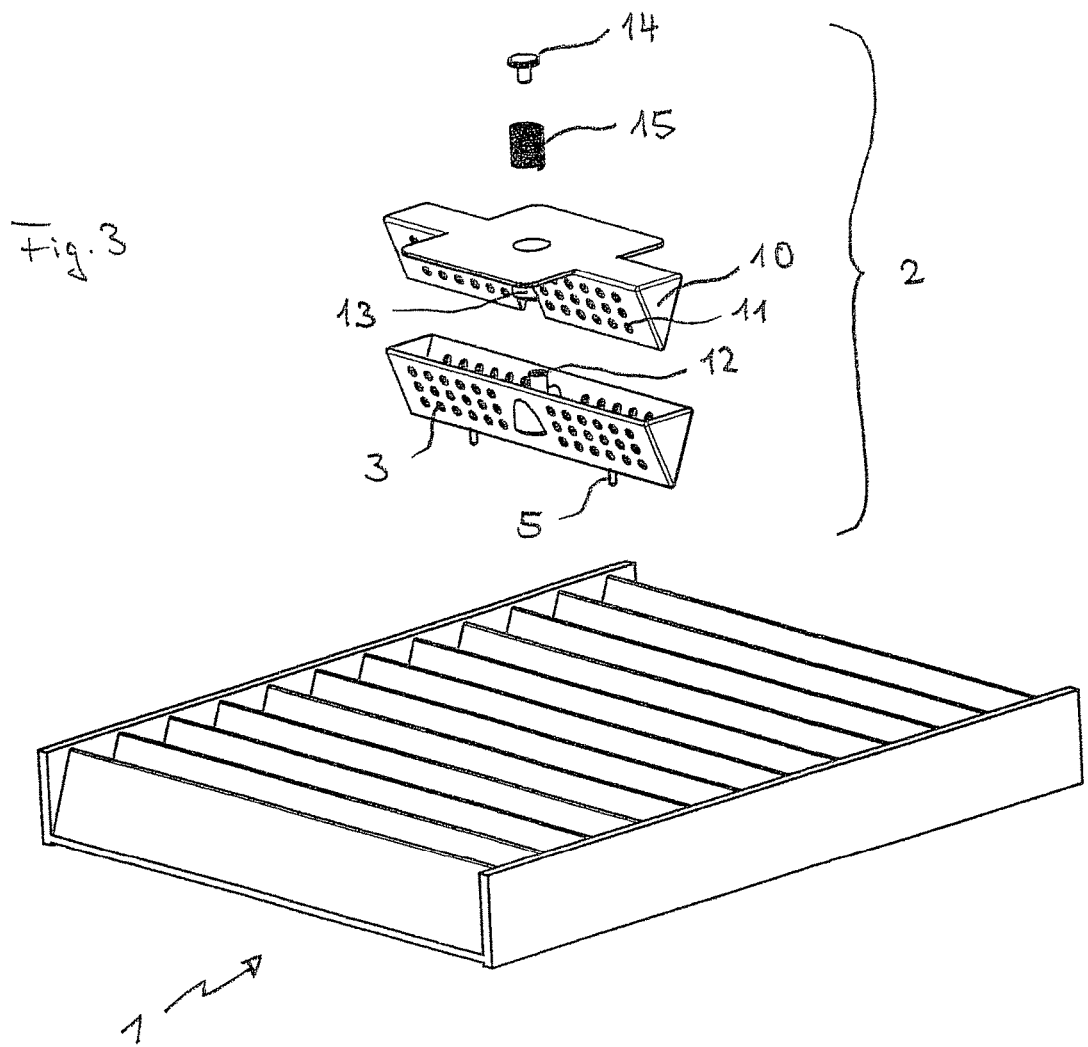

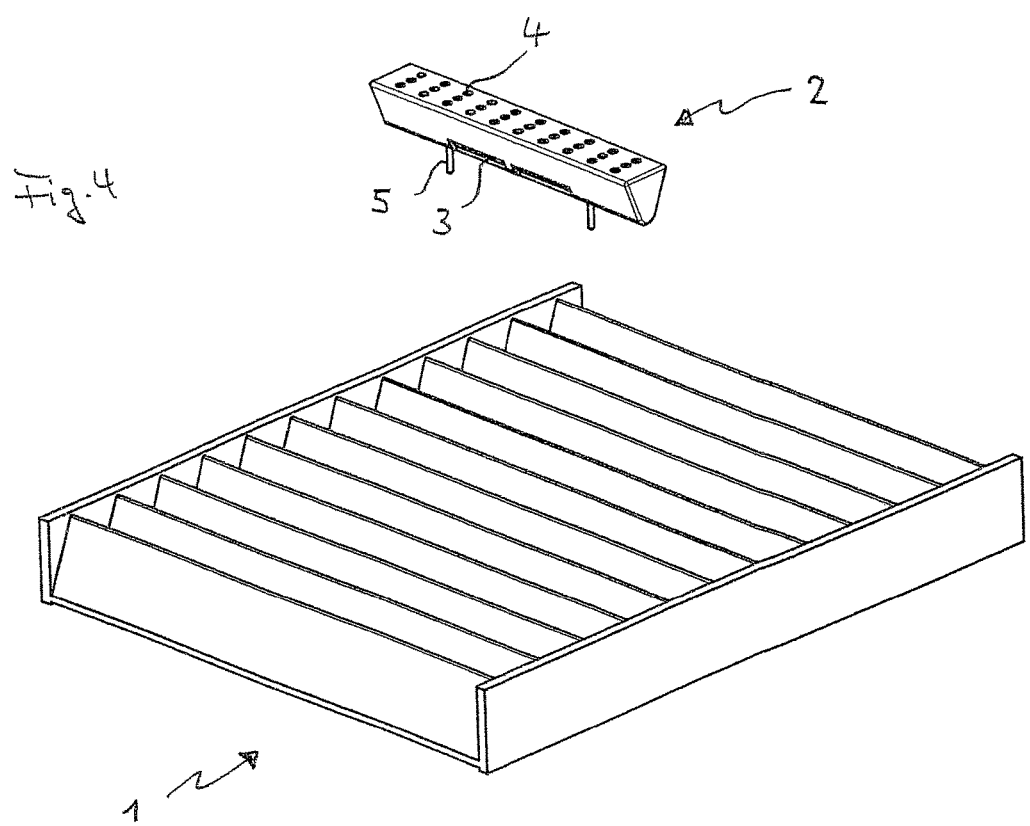

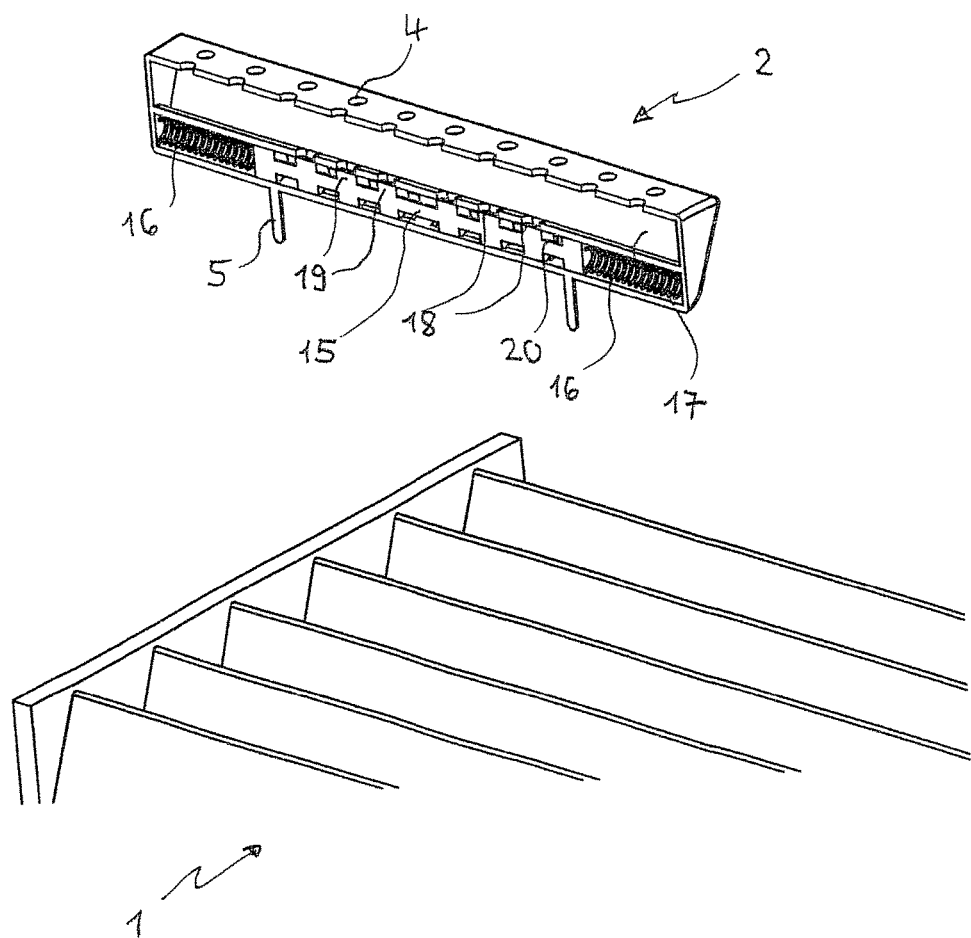

SYSTEM FOR INTRODUCING FRAGRANCES INTO THE INTERIOR OF A VEHICLE

The invention relates to a system for the introduction of fragrances into the interior of a vehicle via the ventilation system, said system comprising a combination of a fragrance cartridge and an air filter, wherein the fragrance cartridge being provided with at least one air inlet opening and at least one air outlet opening as well as a space containing a substrate emitting the fragrance.

The "scenting" of vehicles is to be regarded as standard practice, especially when pre-owned automobiles are intended for resale. Normally, a spray is used for this purpose which enables an interior to be presented to interested parties and buyers inspecting the vehicle that in the first few days and weeks smells freshly and like new. For the same purpose ventilation equipment has been known by means of which a fragrance can be passed into the interior of a motor vehicle. For example, attention is drawn in this context to publications DE 10 2004 017 467 A1 and DE 102 49 305 A1.

The known ventilation systems are primarily intended for refreshing pre-owned automobiles. For fabrication and equipment-related reasons new cars have a "fresh" scent that prevails for a certain period of time. Nevertheless, there are considerations to also equip new cars with a scenting system, on the one hand to counteract off odors arising in or ingressing into the interior of the vehicle from the outside via the ventilation system but also to fill the space with a fragrance that is characteristic of the manufacturer or operator (in the case of rental car companies) in the framework of its "corporate identity" activities.

The prior-art scenting systems hitherto known are either of sophisticated design or function independently of the ventilation system. In the first case, they are expensive and, in the second, they can hardly be controlled and are quickly exhausted because the emanation of the fragrance cannot be interrupted.

It is, therefore, the objective of the present invention to provide a scenting system which is capable of emitting fragrances in a simple and cost-effective way via the ventilation system into the interior space of a vehicle and which is only active when the vehicle is in use or motion and can be renewed in the framework of routine maintenance intervals.

This objective is achieved with a system of the kind first mentioned above by means of which the fragrance cartridge is attached to the air filter of the vehicle in such a manner that air passes through said fragrance cartridge when the ventilation system is in operation.

The inventive system can be put to use in virtually all vehicles that are equipped with a ventilation system and with an air filter for the ventilation system. The ventilation system can be controlled in a limited way by the users of the vehicle so that it conveys a constant flow of fresh air via the ventilation filter into the interior of the vehicle when the vehicle is in motion or the ventilation system has been activated. The combination consisting of fragrance cartridge and ventilation filter makes sure the scenting substances the cartridge contains are entering the interior space of the vehicle together with the fresh air.

The term vehicle shall be understood to include enclosed vehicles such as passenger cars, motortrucks, motorbuses as well as trains and streetcars, i.e. vehicles that are provided with a ventilation system.

The fragrance cartridge proposed by the present invention is provided with at least one air inlet opening and at least one air outlet opening as well as a space arranged in between which accommodates the substrate emanating the scenting substance. Preferably, a fragrance-accommodating porous granular material is employed as substrate. Granular materials of this type are commercially available with a plurality of fragrances.

In the inventive system the fragrance cartridge is firmly anchored to the air filter of the ventilation system. This ensures deposits are prevented from developing between the fragrance cartridge and the ventilation filter. Arranging the fragrance cartridge downstream of the air filter, which is the preferred arrangement, results in the filtered air directly entering the fragrance cartridge where it absorbs the fragrance substance.

The firm anchorage of the fragrance cartridge on the one hand permits air filter and fragrance cartridge to be easily replaced together, for example during the vehicle's maintenance service, but on the other also rules out the fragrance cartridge can slip out of place, be displaced into the ventilation ducts, or even assumes a position where it is no longer passed through by the air flow. This anchoring system may, for example, consist of plug-type connectors, for instance holding bars, with barbs if expedient and necessary, by means of which the cartridge is stuck onto the filter element.

It is to be understood that the fragrance cartridge only covers a small portion of the filter. For the scenting of a vehicle only a limited amount of fragrance substance is needed. For example, it may be sufficient for this purpose to arrange such a fragrance cartridge in one of the pleats of a pleated filter of customary construction. Pleated-paper filters are typically used in motor vehicles and are seen as a preferred filter design for inventive purposes.

The fragrance cartridge to be used according to the invention is preferably attached to the filter in a form-closed manner, for example by means of the plug-type connectors described hereinbefore. Form-closed in this case shall mean that the filter element, and in particular the triangle of a filter pleat, has close contact with the fragrance cartridge. The filtered stream of air that leaves the filter can now enter the fragrance cartridge via the entire contact area and through the openings behind, pass through the fragrance emitting substrate, and, having absorbed the fragrance, exit the cartridge. In this way, the air flow is passed and guided through the fragrance cartridge in a forced manner.

In the embodiment described hereinbefore which provides for the fragrance cartridge to be located downstream of the filter, said cartridge has an essentially triangular form, wherein two sides serve as air intake and the third one as air outlet.

It is considered expedient for the fragrance cartridge to be equipped such that the passage of air takes place in a controlled manner. Such a controlled passage of air shall in particular ensure that an activation of the fragrance cartridge is exclusively brought about when the vehicle is in use. To achieve this, there are several options that may be adopted alternatively or cumulatively.

One option is to provide for various fragrance cartridge openings to be covered by a film/sheet, the segments of which are removable. When not in use, i.e. before the cartridge is mounted in the inventive system, the loss of fragrance can thus be avoided. After mounting, segments of the film/sheet can be removed from the openings as desired so that the degree of fragrance emission can be determined in this way.

This essentially passive system which allows fragrance substances to be released even when the vehicle is inoperative can be supplemented by an active control system making sure the fragrance cartridge is exclusively activated when the vehicle is in operational state. Operational state in this context shall be mean that either the ventilation system is switched on or the vehicle is in operation and a minimum flow of air through the ventilation system is ensured by forced ventilation.

A control feature can be brought about by mounting an element slidable under pressure or a pressure-sensitive membrane arranged especially on the air outlet opening. Such a membrane may span, for example, the air outlet opening and is designed to show one or several incisions, for instance in the form of one or several stars that will close off the opening in nonoperating state but open it when air pressure is applied. Another design option is to arrange a slide closing off the air intake openings in nonoperating state and when the vehicle is in motion being displaced to such an extent that the air intake opening is cleared allowing air to enter the system. For this purpose, said slide may be arranged, for instance, on a central air inlet opening and kept in position on both sides with the aid of springs. Under the influence of centrifugal forces as they are especially experienced when the vehicle is cornering or going around bends the slide is temporarily displaced causing the ventilation path to be cleared. This will usually be sufficient for scenting the interior of a vehicle.

It goes without saying that such a spring mounted slide which is activated by centrifugal force can be combined with a pressure-sensitive membrane located on the air outlet side.

Other control systems are conceivable as well: for example circular openings arranged on the air inlet side that can be kept closed by slidably supported spheres or balls.

It shall also be understood that regulating and controlling the release of fragrances may as well be achieved by means of a motor interacting with the fragrance cartridge. To this end, the fragrance cartridge of the system is provided with one or several slides or flaps which are capable of closing off and/or clearing the openings for air inlet and/or air outlet. The slides and/or flaps are coupled with a small motor capable of moving the slide from close to open position and vice versa. Intermediate positions should also be possible. The motor is connected to the electrical system of the motor car and can be controlled via the vehicles' on-board computer. The same applies to a flap system that can be opened and closed by means of a motor.

The control may in particular be also effected via a microdrive integrated into the cartridge. Such microdrives are employed for example in the field of camera technology. It goes without saying that the cartridge is interface connected for this purpose to the on-board computer and the electric system of the car.

The invention moreover relates to a fragrance cartridge for the system described hereinbefore for the introduction of fragrances into the interior of a vehicle, wherein said cartridge being connected to the air filter of the ventilation system and provided with at least one air inlet opening and at least one air outlet opening as well as a space containing a substrate emitting the fragrance. Said fragrance cartridge is provided with retaining elements for attachment to an air filter, preferably with one or several plug-type connectors which are provided with barbs and can be pushed/pierced through the air filter. Preferably, the fragrance cartridge has a triangular shape so that it fits into the pleats of a pleated filter in a form-closed manner. Expediently, the retaining elements are arranged on the air inlet side of the fragrance cartridge.

The fragrance cartridge is preferably provided with a pressure-sensitive membrane, especially on the side where the air outlet openings are located. The membrane is designed such that it permits the air flow path to be cleared when the ventilation pressure is applied. This may, for example, be achieved by making (for instance star-shaped) incisions into the membrane that open up when airflow pressure is exerted and close when the airflow pressure is missing.

Alternatively or additionally, the fragrance cartridge may be provided with a slider system on the air inlet side that closes the air inlet openings in nonoperating state but clears them when shifted. For example, the slider system is shifted to the clear position by centrifugal force so that it clears the air path when the vehicle moves around curves. To make sure it returns to its resting/closing position such a slide can be supported by and between two spring elements. In such a slider system the air inlet openings are located in the center portion of the fragrance cartridge.

As explained above, the fragrance cartridge may be provided with an integrated micromotor that is capable of operating a slider or flap-type system also existing in the fragrance cartridge and in this way clears, clears to some extent only, or blocks the passage of air. Such a micromotor is disposed of together with the cartridge. It is of course clear that the respective electrical connection systems are also in place.

In the event an external motor is provided, the fragrance cartridge is equipped with the required coupling systems via which a slider or flap-type system can be operated by said externally arranged motor.

Moreover, the invention also relates to a fragrance cartridge that is made available with airtight sealing means for transportation and storage purposes. For this purpose it may, for example, be taped by film/sheet material that is removed prior to use or it may be shrink-wrapped into a plastic bag.

A variety of scents can be available for the fragrance cartridges to be mounted. There is also a possibility to equip a filter insert with several fragrance cartridges of different scent variants of which only a single one is activated at a given time according to preference.

The invention eventually relates to a combination of fragrance cartridge and air filter, in particular as a readily installable replacement element.

The invention is explained in more detail by way of the enclosed figures where

FIG. 1 shows a filter and a fragrance cartridge for the constant dosing of fragrances;

FIG. 2 shows a filter provided with a fragrance cartridge for the volume flow dependent dosing of fragrances;

FIG. 3 a part view of the fragrance cartridge illustrated in FIG. 2;

FIG. 4 illustrates a centrifugally controlled variant of the fragrance cartridge with filter; and FIG. 5 is a cutaway view of the fragrance cartridge illustrated in FIG. 4.

A simple variant of the inventive system is illustrated in FIG. 1 showing a customary pleated filter 1 and a fragrance cartridge 2. The pleated filter 1 consists of a customary filter material suitable for intercepting dust, soot, pollen, as well as other undesirable particles. The filter element usually consists of a nonwoven fabric arranged in pleats and fitted into a suitable slide-in module to be located in the ventilation system.

The outer contour of fragrance cartridge 2 is designed to match the shape of the pleated filter in such a manner that the air inlet sides of the cartridge are in contact in a form-closed manner with the pleats of the filter. Openings 3 are arranged on the air inlet sides through which filtered air is permitted to enter the cartridge. Two plug-type connectors 5 are stuck through the nonwoven fabric and serve to keep the fragrance cartridge in position. Inside the fragrance cartridge 2 there is a space filled with the fragrance-accommodating substrate that preferably consists of a porous polymeric granular material. On the free side air outlet openings 4 are located through which the fragrance-laden filtered air is discharged.

As can be seen above the activated cartridge, the cartridge that is not in use has been sealed with film/sheet in the area of its inlet and outlet openings. In the case illustrated, the openings have been taped with a plurality of film strips 6 that are all provided with handling means 7. Handling means 7 serve to peel off the film strips that at the discretion of the user may be removed individually or altogether so that the degree of the fragrance load admitted to the fresh air can be determined as desired. The higher the air flow rate, the higher the release of fragrance.

FIG. 2 shows another variant of the ventilation system proposed by the present invention with pleated filter 1 and fragrance cartridge 2 which in this case enables the fragrance to be released dependent on the ventilation pressure. Same as the one shown in FIG. 1 the cartridge is provided with inlet openings 3 and plug-type connector 5 but has only one air outlet opening 4 arranged in the cover 8. Cover 8 is provided with wings 9 extending laterally beyond the edge of cartridge 2.

The design of the interior of the cartridge shown in FIG. 2 can be seen from FIG. 3. The cartridge 2 has an insert 10 in which air inlet openings 11 have been provided same as arranged in the cartridge 2 proper. Inside the cartridge 2 a guide tube 12 is arranged that interacts with guide 13 of the insert 10. Guide 13 in turn has a connection to the interior space of insert 10 and serves as air outlet opening. The fragrance-laden granular material is located in insert 10.

Insert 10 itself is secured mechanically to holding element 12 in cartridge 2 by means of screw 14 and guide sleeve 15 so that the insert 10 can be shifted in vertical direction.

In nonoperating state the insert 10 is supported by cartridge 2 such that, air inlet openings 3 and 11 are in offset position which prevents ventilation air from passing through. When the vehicle is in motion and fan activated causing ventilation pressure to be exerted the insert 10 is lifted upwards, also due to the air pressure acting on wings 9, resulting in the inlet openings 3 and 11 to coincide. Air is now allowed to enter insert 10, passes through the granular material, and via the outlet opening 4 flows into the interior of the vehicle.

In FIG. 4 another variant of the inventive system is illustrated, wherein cartridge 2 is provided with lateral air inlet openings 3 of slotted shape and a plurality of air outlet openings 4 arranged on the top side. Plug-type connectors 5 are provided here as well.

The functioning of the fragrance cartridge shown in FIG. 4 is explained by way of FIG. 5 illustrating the fragrance cartridge 2 in pass-through state. In the lower area of cartridge 2 a slider system 15 is arranged which has spring elements 16 on both sides. The spring elements 16 abut against the end walls of fragrance cartridge 2.

Inside the cartridge 2 there is a space 17 which accommodates the fragrance-laden granular material. In the lower area, said space 17 is provided with openings 18 corresponding with the closure elements 19 of the slide 15. In the nonoperating state of slide 15 the openings 19 are blocked by means of the closure elements 18. However, when the vehicle moves around curves the slide 15 is shifted by centrifugal force to either side as the case may be thus clearing openings 18 via the cutouts 20 located between the closure elements 19 so that air is permitted to enter into the granular material through the laterally arranged inlet openings 3 and openings 18, and exit through the outlet opening 4 to pass into the interior of the vehicle.

In the embodiment shown in FIGS. 4/5 the slider function may alternatively be controlled by means of a motor. In that case, the slide is not shifted by the movement the vehicle performs but through the motor the driver actuates according to his/her needs via the on-board electronic system. Such a motor enables the fragrance cartridge to be completely closed off but as well its complete opening and intermediate settings. Said motor may be a micromotor integrated into the cartridge or an external motor causing the slide to be shifted via a coupling rod.

The invention claimed is:

1. System for introducing fragrances into the interior of a vehicle via the ventilation system comprising a combination of a fragrance cartridge (2) and an air filter (1), wherein the fragrance cartridge (2) has at least one air inlet opening (3) and at least one air outlet opening (4), as well as a space (17) accommodating a fragrance-emanating substrate, characterized in that the fragrance cartridge (2) is secured to the air filter (1) in such a manner that air is allowed to pass through the fragrance cartridge (2) when the ventilation system has been activated, the fragrance cartridge being equipped with one or several slides (15) or flaps closing off or clearing the air inlet openings (3) or air outlet openings (4) or both and having an insert (10) holding the fragrance-emanating substrate, the insert (10) being secured mechanically to a holding element (12) in cartridge (2) by means of a screw (14) and a guide sleeve (15) so that the insert (10) can be shifted in a vertical direction.

2. System according to claim 1, characterized in that the fragrance cartridge (2) is arranged downstream of the air filter (1).

3. System according to claim 1, characterized in that the fragrance cartridge (2) is filled with a fragrance-laden granular material.

4. System according to claim 1, characterized in that the air filter (1) is a pleated filter.

5. System according to claim 1, characterized in that the fragrance cartridge (2) is attached to the air filter in a form-closed manner via a plug-type connection (5).

6. System according to claim 1, characterized by a pressure-sensitive element (8) of the fragrance cartridge (2) clearing the passage when ventilation pressure is applied.

* * * * *